(12) United States Patent
Markowitz et al.

(10) Patent No.: US 8,839,798 B2
(45) Date of Patent: Sep. 23, 2014

(54) SYSTEM AND METHOD FOR DETERMINING SHEATH LOCATION

(75) Inventors: H. Toby Markowitz, Roseville, MN (US); Chad Giese, St. Paul, MN (US); Jeff Jannicke, Andover, MN (US); Steven L. Waldhauser, White Bear Township, MN (US)

(73) Assignee: Medtronic, Inc., Minneapolis, MN (US)

( * ) Notice: Subject to any disclaimer, the term of this patent is extended or adjusted under 35 U.S.C. 154(b) by 1135 days.

(21) Appl. No.: 12/421,375

(22) Filed: Apr. 9, 2009

(65) Prior Publication Data

US 2009/0264739 A1 Oct. 22, 2009

(51) Int. Cl.
*A61B 19/00* (2006.01)

(52) U.S. Cl.
USPC ............................................ 128/897

(58) Field of Classification Search
USPC .......... 128/897, 899; 600/372, 424, 373, 382, 600/547; 606/129
See application file for complete search history.

(56) References Cited

U.S. PATENT DOCUMENTS

| | | | |
|---|---|---|---|
| 3,661,157 | A | 5/1972 | Fyson et al. |
| 3,837,347 | A | 9/1974 | Tower |
| 3,995,623 | A | 12/1976 | Blake et al. |
| 4,506,680 | A | 3/1985 | Stokes |
| 4,619,246 | A | 10/1986 | Molgaard-Nielsen et al. |
| 4,649,924 | A | 3/1987 | Taccardi |
| 4,696,304 | A | 9/1987 | Chin |
| 4,801,297 | A | 1/1989 | Mueller |
| 4,852,580 | A * | 8/1989 | Wood ............................ 600/506 |
| 5,035,246 | A | 7/1991 | Heuvelmans et al. |
| 5,076,285 | A | 12/1991 | Hess et al. |
| 5,078,714 | A | 1/1992 | Katims |

(Continued)

FOREIGN PATENT DOCUMENTS

| | | |
|---|---|---|
| CN | 101711125 A | 5/2010 |
| CN | 102056537 A | 5/2011 |

(Continued)

OTHER PUBLICATIONS

Birkfellner, Wolfgang, et al. "Calibration of Tracking Systems in a Surgical Environment," IEEE Transactions on Medical Imaginge, IEEE Service Center, Piscataway, NJ, US, vol. 17, No. 5. (Oct. 1, 1998) XP011035767. ISSN: 0278-0062 the whole document.

(Continued)

*Primary Examiner* — Christine Matthews
*Assistant Examiner* — Shannon McBride
(74) *Attorney, Agent, or Firm* — Harness, Dickey

(57) ABSTRACT

A system for determining a location of an instrument within an anatomy is provided. The system can include a first instrument, which can define at least one lumen. The system can further include a second instrument, which can be received through the at least one lumen. The system can include at least one electrode, which can be coupled to a distal end of the first instrument. The electrode can be responsive to electrical activity to generate at least one signal. The system can include a sensing unit, which can be in contact with the anatomy to sense electrical activity within the anatomy at a location near the instrument. The sensing unit can be in communication with the electrode to receive the signal. The system can further include a control module that can determine, based on the sensed electrical activity and the signal, the location of the first instrument.

24 Claims, 7 Drawing Sheets

(56) References Cited

U.S. PATENT DOCUMENTS

| | | |
|---|---|---|
| 5,099,845 A | 3/1992 | Besz et al. |
| 5,146,414 A | 9/1992 | McKown et al. |
| 5,167,239 A | 12/1992 | Cohen et al. |
| 5,255,680 A | 10/1993 | Darrow et al. |
| 5,265,622 A | 11/1993 | Barbere |
| 5,297,549 A | 3/1994 | Beatty et al. |
| 5,342,295 A | 8/1994 | Imran |
| 5,385,148 A | 1/1995 | Lesh et al. |
| 5,391,199 A | 2/1995 | Ben-Haim |
| 5,403,311 A | 4/1995 | Abele et al. |
| 5,443,489 A | 8/1995 | Ben-Haim |
| 5,480,422 A | 1/1996 | Ben-Haim |
| 5,512,920 A | 4/1996 | Gibson |
| 5,522,874 A | 6/1996 | Gates |
| 5,538,007 A | 7/1996 | Gorman |
| 5,546,951 A | 8/1996 | Ben-Haim |
| 5,558,091 A | 9/1996 | Acker et al. |
| 5,568,809 A | 10/1996 | Ben-haim |
| 5,592,939 A | 1/1997 | Martinelli |
| 5,598,848 A | 2/1997 | Swanson et al. |
| 5,601,084 A | 2/1997 | Sheehan et al. |
| 5,639,276 A | 6/1997 | Weinstock et al. |
| 5,697,377 A | 12/1997 | Wittkampf |
| 5,713,946 A | 2/1998 | Ben-Haim |
| 5,797,849 A | 8/1998 | Vesely et al. |
| 5,800,407 A | 9/1998 | Eldor et al. |
| 5,840,025 A | 11/1998 | Ben-Haim |
| 5,916,193 A | 6/1999 | Stevens et al. |
| 5,944,022 A | 8/1999 | Nardella et al. |
| 5,983,126 A | 11/1999 | Wittkampf |
| 6,009,349 A | 12/1999 | Mouchawar et al. |
| 6,016,447 A | 1/2000 | Juran et al. |
| 6,050,267 A | 4/2000 | Nardella et al. |
| 6,088,527 A | 7/2000 | Rybczynski |
| 6,090,105 A | 7/2000 | Zepeda et al. |
| 6,122,552 A | 9/2000 | Tockman et al. |
| 6,152,946 A | 11/2000 | Broome et al. |
| 6,196,230 B1 | 3/2001 | Hall et al. |
| 6,226,547 B1 | 5/2001 | Lockhart et al. |
| 6,236,886 B1 | 5/2001 | Cherepenin et al. |
| 6,240,307 B1 | 5/2001 | Beatty et al. |
| 6,246,468 B1 | 6/2001 | Dimsdale |
| 6,256,121 B1 | 7/2001 | Lizotte et al. |
| 6,301,498 B1 | 10/2001 | Greenberg et al. |
| 6,330,356 B1 | 12/2001 | Sundareswaran et al. |
| 6,389,187 B1 | 5/2002 | Greenaway et al. |
| 6,470,205 B2 | 10/2002 | Bosselmann et al. |
| 6,490,474 B1 | 12/2002 | Willis et al. |
| 6,527,782 B2 | 3/2003 | Hogg et al. |
| 6,546,270 B1 | 4/2003 | Goldin et al. |
| 6,569,159 B1 | 5/2003 | Edwards et al. |
| 6,569,160 B1 | 5/2003 | Goldin et al. |
| 6,574,498 B1 | 6/2003 | Gilboa |
| 6,595,989 B1 | 7/2003 | Schaer |
| 6,602,271 B2 | 8/2003 | Adams et al. |
| 6,611,141 B1 | 8/2003 | Schulz et al. |
| 6,611,705 B2 | 8/2003 | Hopman et al. |
| 6,701,176 B1 | 3/2004 | Halperin et al. |
| 6,714,806 B2 | 3/2004 | Iaizzo et al. |
| 6,771,996 B2 | 8/2004 | Bowe et al. |
| 6,868,195 B2 | 3/2005 | Fujita et al. |
| 6,888,623 B2 | 5/2005 | Clements |
| 6,892,091 B1 | 5/2005 | Ben-Haim et al. |
| 6,898,302 B1 | 5/2005 | Brummer |
| 6,990,370 B1 | 1/2006 | Beatty et al. |
| 7,020,522 B1 | 3/2006 | Hoijer et al. |
| 7,047,073 B2 | 5/2006 | Hoijer et al. |
| 7,089,045 B2 | 8/2006 | Fuimaono et al. |
| 7,189,208 B1 | 3/2007 | Beatty et al. |
| 7,207,989 B2 | 4/2007 | Pike, Jr. et al. |
| 7,215,430 B2 | 5/2007 | Kacyra et al. |
| 7,263,397 B2 | 8/2007 | Hauck et al. |
| 7,305,121 B2 | 12/2007 | Kaufmann et al. |
| 7,328,071 B1 | 2/2008 | Stehr et al. |
| 7,369,901 B1 | 5/2008 | Morgan et al. |
| 7,421,300 B2 | 9/2008 | Smits et al. |
| 7,479,141 B2 | 1/2009 | Kleen et al. |
| 7,529,584 B2 | 5/2009 | Laske et al. |
| 7,686,757 B2 | 3/2010 | Minai |
| 7,715,604 B2 | 5/2010 | Sun et al. |
| 7,824,328 B2 | 11/2010 | Gattani et al. |
| 7,848,787 B2 | 12/2010 | Osadchy |
| 7,941,213 B2 | 5/2011 | Markowitz et al. |
| 7,988,639 B2 | 8/2011 | Starks |
| 8,106,905 B2 | 1/2012 | Markowitz et al. |
| 8,135,467 B2 | 3/2012 | Markowitz et al. |
| 8,155,756 B2 * | 4/2012 | Yang et al. .................. 607/116 |
| 8,175,681 B2 | 5/2012 | Hartmann et al. |
| 8,185,192 B2 | 5/2012 | Markowitz et al. |
| 8,208,991 B2 | 6/2012 | Markowitz et al. |
| 8,214,018 B2 | 7/2012 | Markowitz et al. |
| 8,224,456 B2 | 7/2012 | Daglow et al. |
| 8,239,001 B2 | 8/2012 | Verard et al. |
| 8,260,395 B2 | 9/2012 | Markowitz et al. |
| 8,340,751 B2 | 12/2012 | Markowitz et al. |
| 8,345,067 B2 | 1/2013 | Markowitz et al. |
| 8,355,774 B2 | 1/2013 | Markowitz et al. |
| 8,364,252 B2 | 1/2013 | Markowitz et al. |
| 8,391,965 B2 | 3/2013 | Markowitz et al. |
| 8,401,616 B2 | 3/2013 | Verard et al. |
| 8,421,799 B2 | 4/2013 | Markowitz et al. |
| 8,424,536 B2 | 4/2013 | Markowitz et al. |
| 8,442,625 B2 | 5/2013 | Markowitz et al. |
| 8,457,371 B2 | 6/2013 | Markowitz et al. |
| 8,494,608 B2 | 7/2013 | Markowitz et al. |
| 8,494,614 B2 | 7/2013 | Markowitz et al. |
| 8,532,734 B2 | 9/2013 | Markowitz et al. |
| 2001/0000800 A1 * | 5/2001 | Partridge et al. .............. 607/130 |
| 2001/0031920 A1 | 10/2001 | Kaufman et al. |
| 2002/0038094 A1 | 3/2002 | Gorman |
| 2002/0045810 A1 | 4/2002 | Ben-Haim |
| 2002/0049375 A1 | 4/2002 | Strommer et al. |
| 2002/0077544 A1 | 6/2002 | Shahidi |
| 2002/0111662 A1 | 8/2002 | Iaizzo et al. |
| 2002/0147488 A1 | 10/2002 | Doan et al. |
| 2002/0183817 A1 | 12/2002 | Van Venrooij et al. |
| 2003/0028118 A1 | 2/2003 | Dupree et al. |
| 2003/0055324 A1 | 3/2003 | Wasserman |
| 2003/0078494 A1 | 4/2003 | Panescu et al. |
| 2003/0100821 A1 | 5/2003 | Heller et al. |
| 2003/0108853 A1 | 6/2003 | Chosack et al. |
| 2003/0114908 A1 | 6/2003 | Flach |
| 2003/0225434 A1 | 12/2003 | Glantz et al. |
| 2003/0231789 A1 | 12/2003 | Willis et al. |
| 2004/0001075 A1 | 1/2004 | Balakrishnan et al. |
| 2004/0019318 A1 | 1/2004 | Wilson et al. |
| 2004/0019359 A1 * | 1/2004 | Worley et al. .................. 606/129 |
| 2004/0044295 A1 | 3/2004 | Reinert et al. |
| 2004/0064159 A1 | 4/2004 | Hoijer et al. |
| 2004/0068312 A1 | 4/2004 | Sigg et al. |
| 2004/0070582 A1 | 4/2004 | Smith et al. |
| 2004/0097805 A1 | 5/2004 | Verard et al. |
| 2004/0097806 A1 * | 5/2004 | Hunter et al. .................. 600/434 |
| 2004/0162599 A1 | 8/2004 | Kurth |
| 2004/0199082 A1 | 10/2004 | Ostroff et al. |
| 2004/0215298 A1 | 10/2004 | Richardson et al. |
| 2004/0228453 A1 | 11/2004 | Dobbs et al. |
| 2004/0236395 A1 | 11/2004 | Iaizzo et al. |
| 2004/0249281 A1 | 12/2004 | Olstad |
| 2004/0249430 A1 | 12/2004 | Martinez et al. |
| 2004/0254437 A1 | 12/2004 | Hauck et al. |
| 2005/0004476 A1 | 1/2005 | Payvar et al. |
| 2005/0018888 A1 | 1/2005 | Zonneveld |
| 2005/0119550 A1 | 6/2005 | Serra et al. |
| 2005/0177151 A1 | 8/2005 | Coen et al. |
| 2005/0187432 A1 | 8/2005 | Hale et al. |
| 2005/0245803 A1 | 11/2005 | Glenn Jr. et al. |
| 2005/0288586 A1 | 12/2005 | Ferek-Petric |
| 2006/0013523 A1 | 1/2006 | Childers et al. |
| 2006/0058604 A1 | 3/2006 | Avinash et al. |
| 2006/0116576 A1 | 6/2006 | McGee et al. |
| 2006/0117773 A1 | 6/2006 | Street et al. |
| 2006/0135883 A1 | 6/2006 | Jonsson et al. |
| 2006/0153468 A1 | 7/2006 | Solf et al. |

(56) References Cited

U.S. PATENT DOCUMENTS

| | | |
|---|---|---|
| 2006/0173268 A1 | 8/2006 | Mullick et al. |
| 2006/0173381 A1 | 8/2006 | Eck |
| 2006/0200049 A1 | 9/2006 | Leo et al. |
| 2006/0206157 A1 | 9/2006 | Hoijer |
| 2006/0229513 A1 | 10/2006 | Wakai |
| 2006/0229594 A1 | 10/2006 | Francischelli et al. |
| 2006/0247520 A1 | 11/2006 | McGee |
| 2006/0253116 A1 | 11/2006 | Avitall et al. |
| 2007/0016084 A1 | 1/2007 | Denault |
| 2007/0038052 A1 | 2/2007 | Swoyer et al. |
| 2007/0043413 A1 | 2/2007 | Eversull et al. |
| 2007/0046661 A1 | 3/2007 | Ma et al. |
| 2007/0049817 A1 | 3/2007 | Preiss et al. |
| 2007/0060833 A1 | 3/2007 | Hauck |
| 2007/0066889 A1 | 3/2007 | Boese et al. |
| 2007/0112388 A1 | 5/2007 | Salo |
| 2007/0123944 A1 | 5/2007 | Zdeblick |
| 2007/0135721 A1 | 6/2007 | Zdeblick |
| 2007/0135803 A1 | 6/2007 | Belson |
| 2007/0156019 A1 | 7/2007 | Larkin et al. |
| 2007/0156132 A1* | 7/2007 | Drysen ............ 606/41 |
| 2007/0164900 A1 | 7/2007 | Schneider et al. |
| 2007/0167801 A1 | 7/2007 | Webler et al. |
| 2007/0232898 A1 | 10/2007 | Huynh et al. |
| 2007/0252074 A1 | 11/2007 | Ng et al. |
| 2007/0255270 A1 | 11/2007 | Carney |
| 2007/0270682 A1 | 11/2007 | Huang et al. |
| 2007/0299351 A1 | 12/2007 | Harlev et al. |
| 2007/0299352 A1 | 12/2007 | Harlev et al. |
| 2007/0299353 A1 | 12/2007 | Harlev et al. |
| 2008/0015466 A1 | 1/2008 | Lerman |
| 2008/0024493 A1 | 1/2008 | Bordoloi et al. |
| 2008/0038197 A1 | 2/2008 | John et al. |
| 2008/0058656 A1 | 3/2008 | Costello et al. |
| 2008/0071142 A1 | 3/2008 | Gattani et al. |
| 2008/0103535 A1 | 5/2008 | Ostroff et al. |
| 2008/0118117 A1 | 5/2008 | Gauldie et al. |
| 2008/0123910 A1 | 5/2008 | Zhu |
| 2008/0132800 A1 | 6/2008 | Hettrick et al. |
| 2008/0183072 A1 | 7/2008 | Robertson et al. |
| 2008/0207997 A1 | 8/2008 | Higgins et al. |
| 2008/0221425 A1 | 9/2008 | Olson et al. |
| 2008/0221438 A1 | 9/2008 | Chen et al. |
| 2008/0243025 A1 | 10/2008 | Holmstrom et al. |
| 2008/0249375 A1 | 10/2008 | Obel |
| 2008/0255470 A1 | 10/2008 | Hauck et al. |
| 2008/0319297 A1 | 12/2008 | Danehorn |
| 2009/0017430 A1 | 1/2009 | Muller-Daniels et al. |
| 2009/0063118 A1 | 3/2009 | Dachille et al. |
| 2009/0093857 A1 | 4/2009 | Markowitz et al. |
| 2009/0099619 A1 | 4/2009 | Lessmeier et al. |
| 2009/0103793 A1 | 4/2009 | Borland et al. |
| 2009/0126575 A1 | 5/2009 | Son et al. |
| 2009/0129477 A1 | 5/2009 | Yang |
| 2009/0131955 A1 | 5/2009 | Wenderow et al. |
| 2009/0192381 A1 | 7/2009 | Brockway et al. |
| 2009/0211909 A1 | 8/2009 | Nesbitt |
| 2009/0227861 A1 | 9/2009 | Ganatra et al. |
| 2009/0253976 A1 | 10/2009 | Harlev et al. |
| 2009/0253985 A1 | 10/2009 | Shachar et al. |
| 2009/0262109 A1 | 10/2009 | Markowitz et al. |
| 2009/0262979 A1 | 10/2009 | Markowitz et al. |
| 2009/0262980 A1 | 10/2009 | Markowitz et al. |
| 2009/0262982 A1 | 10/2009 | Markowitz et al. |
| 2009/0262992 A1 | 10/2009 | Markowitz et al. |
| 2009/0264727 A1 | 10/2009 | Markowitz et al. |
| 2009/0264738 A1 | 10/2009 | Markowitz et al. |
| 2009/0264739 A1 | 10/2009 | Markowitz et al. |
| 2009/0264740 A1 | 10/2009 | Markowitz et al. |
| 2009/0264741 A1 | 10/2009 | Markowitz et al. |
| 2009/0264742 A1 | 10/2009 | Markowitz et al. |
| 2009/0264743 A1 | 10/2009 | Markowitz et al. |
| 2009/0264744 A1 | 10/2009 | Markowitz et al. |
| 2009/0264745 A1 | 10/2009 | Markowitz et al. |
| 2009/0264746 A1 | 10/2009 | Markowitz et al. |
| 2009/0264747 A1 | 10/2009 | Markowitz et al. |
| 2009/0264748 A1 | 10/2009 | Markowitz et al. |
| 2009/0264749 A1 | 10/2009 | Markowitz et al. |
| 2009/0264750 A1 | 10/2009 | Markowitz et al. |
| 2009/0264751 A1 | 10/2009 | Markowitz et al. |
| 2009/0264752 A1 | 10/2009 | Markowitz et al. |
| 2009/0264777 A1 | 10/2009 | Markowitz et al. |
| 2009/0264778 A1 | 10/2009 | Markowitz et al. |
| 2009/0265128 A1 | 10/2009 | Markowitz et al. |
| 2009/0267773 A1 | 10/2009 | Markowitz et al. |
| 2009/0297001 A1 | 12/2009 | Markowitz et al. |
| 2009/0306732 A1 | 12/2009 | Rosenberg et al. |
| 2010/0004724 A1 | 1/2010 | Markowitz et al. |
| 2010/0030298 A1 | 2/2010 | Martens et al. |
| 2010/0152571 A1 | 6/2010 | Hartmann et al. |
| 2011/0054293 A1 | 3/2011 | Markowitz et al. |
| 2011/0054304 A1 | 3/2011 | Markowitz et al. |
| 2011/0106203 A1 | 5/2011 | Markowitz et al. |
| 2012/0123474 A1 | 5/2012 | Zajac et al. |
| 2012/0123541 A1 | 5/2012 | Albertorio et al. |
| 2012/0130232 A1 | 5/2012 | Markowitz et al. |
| 2012/0190993 A1 | 7/2012 | Markowitz et al. |
| 2012/0220860 A1 | 8/2012 | Hartmann et al. |
| 2012/0226110 A1 | 9/2012 | Markowitz et al. |

FOREIGN PATENT DOCUMENTS

| | | |
|---|---|---|
| CN | 102118994 A | 7/2011 |
| EP | 363117 | 4/1990 |
| EP | 1393674 A1 | 3/2004 |
| EP | 1421913 A1 | 5/2004 |
| EP | 2136706 | 12/2009 |
| EP | 2276402 A1 | 1/2011 |
| WO | WO-9848722 A1 | 11/1998 |
| WO | WO-0134050 A2 | 5/2001 |
| WO | WO-02064040 A2 | 8/2002 |
| WO | WO-2005112836 A2 | 12/2005 |
| WO | WO-2006042039 A2 | 4/2006 |
| WO | WO-2006117773 A1 | 11/2006 |
| WO | WO-2007067945 | 6/2007 |
| WO | WO-2007111542 A1 | 10/2007 |
| WO | WO-2007136451 A2 | 11/2007 |
| WO | WO-2008108901 | 9/2008 |
| WO | WO-2008147961 A1 | 12/2008 |
| WO | WO-2009086392 A1 | 7/2009 |
| WO | WO-2009126575 A1 | 10/2009 |
| WO | WO-2009129475 A1 | 10/2009 |
| WO | WO-2009129477 A1 | 10/2009 |
| WO | WO-2009129484 A1 | 10/2009 |
| WO | WO-2010074986 A1 | 7/2010 |
| WO | WO-2010118314 A1 | 10/2010 |
| WO | WO-2011025708 A2 | 3/2011 |
| WO | WO-2011026077 A2 | 3/2011 |

OTHER PUBLICATIONS

Hubert-Tremblay, Vincent, et al. "Octree indexing of DICOM images for voxel number reduction and improvement of Monte Carolo simulation computing efficiency," Medical Physics, AIP, Melville, NY, US, vol. 33, No. 8, (Jul. 21, 2006) pp. 2819-2831, XP012092212, ISSN: 0094-2405, DOI: 10.1118/1.2214305 pp. 2820-2821.

International Preliminary Report on Patentability mailed Oct. 11, 2011 for PCT/US2010/030534 claming benefit of U.S. Appl. No. 12/421,375, filed Apr. 9, 2009.

International Search Report and Written Opinon mailed Jul. 25, 2011 for PCT/US2010/047241 claiming benefit of U.S. Appl. No. 12/844,065, filed Jul. 27, 2010.

International Search Report mailed Sep. 13, 2010 for PCT/US2010/030534 claming benefit of U.S. Appl. No. 12/421,375, filed Apr. 9, 2009.

Invitation to Pay Additional Fees mailed Jul. 7, 2010 for PCT/US2010/030534 claming benefit of U.S. Appl. No. 12/421,375, filed Apr. 9, 2009.

"EnSite NavX™ Navigation & Visualization Technology." 3 pages, St. Jude Medical. http://www.sjmprofessional.com/Products/US/Mapping-and-Visualization/EnSite-NavX-Navigation-and-Visualization-Technology.aspx Web. Accessed Jun. 19, 2009.

(56) References Cited

OTHER PUBLICATIONS

"Local Lisa® Intracardiac Navigation System Model 9670000/9670025." Technical Manual Version 1.2, Chapter 1, pp. 1-19. 2004.
Brenner, David J., Ph.D., "Computed Tomography—An Increasing Source of Radiation Exposure", The New England Journal of Medicine (Nov. 29, 2007), pp. 2277-2284.
Gepstein, Lior, M.D., "A Novel Method for Nonfluoroscopic Catheter-Based Electroanatomical Mapping of the Heart, In Vitro and In Vivo Accuracy Results", American Heart Association, Learn and Live, Circulation (1997), http://circ.ahajournals.org/cgi/content/abstract/95/6/1611 printed Oct. 2, 2008.
International Preliminary Report on Patentability and Written Opinion for PCT/US2009/040998 mailed Oct. 28, 2010, 2009 claiming benefit of U.S. Appl. No. 12/421,332, filed Apr. 9, 2009; which claims priority to U.S. Appl. No. 61/105,957, filed Oct. 16, 2008; U.S. Appl. No. 12/117,549, filed May 8, 2008.
International Preliminary Report on Patentability and Written Opinion for PCT/US2009/0400984 mailed Oct. 28, 2010, claiming benefit of U.S. Appl. No. 12/117,549, filed May 8, 2008.
International Preliminary Report on Patentability and Written Opinion for PCT/US2009/040979 mailed Oct. 28, 2010 claiming benefit of U.S. Appl. No. 12/117,537, filed May 8, 2008.
International Preliminary Report on Patentability and Written Opinion mailed Oct. 29, 2009 for PCT/US2007/089087, of which U.S. Appl. No. 12/492,906, filed Jun. 26, 2009 claims benefit.
International Search Report and Written Opinion for PCT/US2008/088189 mailed Apr. 3, 2009, claiming benefit of U.S. Appl. No. 12/183,796, filed Jul. 31, 2008; and claims priority to U.S. Appl. No. 11/966,382, filed Dec. 28, 2007.
International Search Report and Written Opinion for PCT/US2009/0400984 mailed Sep. 21, 2009, claiming benefit of U.S. Appl. No. 12/117,549, filed May 8, 2008.
International Search Report and Written Opinion for PCT/US2009/040998 mailed Jul. 29, 2009 claiming benefit of U.S. Appl. No. 12/421,332, filed Apr. 9, 2009; which claims priority to U.S. Appl. No. 61/105,957, filed Oct. 16, 2008; U.S. Appl. No. 12/117,549, filed May 8, 2008.
International Search Report and Written Opinion for PCT/US2009/067486 mailed May 4, 2010, claiming benefit of U.S. Appl. No. 12/336,085, filed Dec. 16, 2008.
International Search Report and Written Opinion mailed Dec. 6, 2010 for PCT/US2010/051248, which claims benefit of U.S. Appl. No. 12/609,734 filed Oct. 30, 2009.
International Search Report and Written Opinon for PCT/US2009/040979 mailed Sep. 21, 2009 claiming benefit of U.S. Appl. No. 12/117,537, filed May 8, 2008.
International Search Report for PCT/US2007/089087 mailed Jul. 9, 2008, of which U.S. Appl. No. 12/492,906, filed Jun. 26, 2009 claims benefit.
Invitation to Pay Additional Fees for PCT/US2009/0400984 mailed Jul. 30, 2009, claiming benefit of U.S. Appl. No. 12/117,549, filed May 8, 2008.
Invitation to Pay Additional Fees for PCT/US2009/040979 mailed Jul. 30, 2009 claiming benefit of U.S. Appl. No. 12/117,537, filed May 8, 2008.
Invitation to Pay Additional Fees for PCT/US2009/067486 mailed Mar. 5, 2010, claiming benefit of U.S. Appl. No. 12/336,085, filed Dec. 16, 2008.
Invitation to Pay Additional Fees for PCT/US2010/047241 mailed Jan. 10, 2011, claiming benefit of U.S. Appl. No. 12/844,065, filed Jul. 27, 2010.
Invitation to Pay Additional Fees mailed Jul. 7, 2010 for PCT/US2010/030534 claiming benefit of U.S. Appl. No. 12/421,375, filed Apr. 9, 2009.
Jiang, Yuan. "An Impedance-Based Catheter Poisitioning System for Cardiac Mapping and Navigation." IEEE Transactions on Biomedical Engineering, (Aug. 2009) pp. 1963-1970, vol. 56, No. 8.
Markowitz, Toby, et al., "Unleaded: The Fluoroless 3D Lead Implant", Presented at Heart Rhythm Society, Denver, CO, (May 2007) 1 pg.
Markowitz, Toby, et al., Abstract Submission, Unleaded: "The Fluoroless 3D Lead Implant", Mar. 2007 2 pgs.
Milstein, S. et al., "Initial Clinical Results of Non-Fluoroscopic Pacemaker Lead Implantation." (pre-presentation abstract) May 14-17, 2008. 2 pgs.
Milstein, S. et al., "Initial Clinical Results of Non-Fluoroscopic Pacemaker Lead Implantation." (poster presentation) May 14-17, 2008. 1 pg.
Nelder, J.A., et al. "A simplex method for function minimization." vol. 7, Issue 4, (1965) pp. 308-313. The Computer Journal.
Savage, George, M.D., "Electric Tomography (ET)—A Novel Method for Assessing Myocardial Motion and Cardiac Performance", Heart Rhytm Society, Denver, CO (May 9-12, 2007) 1 pg.
Wittkampf, Fred, H.M., et al., "LocaLisa: New Technique for Real-Time 3-Dimensional Localization of Regular Intracardiac Electrodes." Circulation Journal of the American Heart Association, 1999; 99; 13-12-1317.
Wittkampf, Fred., H.M., et al. "Accuracy of the LocaLisa System in Catheter Ablation Procedures." Journal of Electrocardiology vol. 32 Supplement (1999). Heart Lung Institute, University Hospital Utrecht, The Netherlands.
International Preliminary Report on Patentability and Written Opinion for PCT/US2010/047241 mailed Mar. 15, 2012 claiming benefit of U.S. Appl. No. 12/844,065, filed Jul. 27, 2010.

* cited by examiner

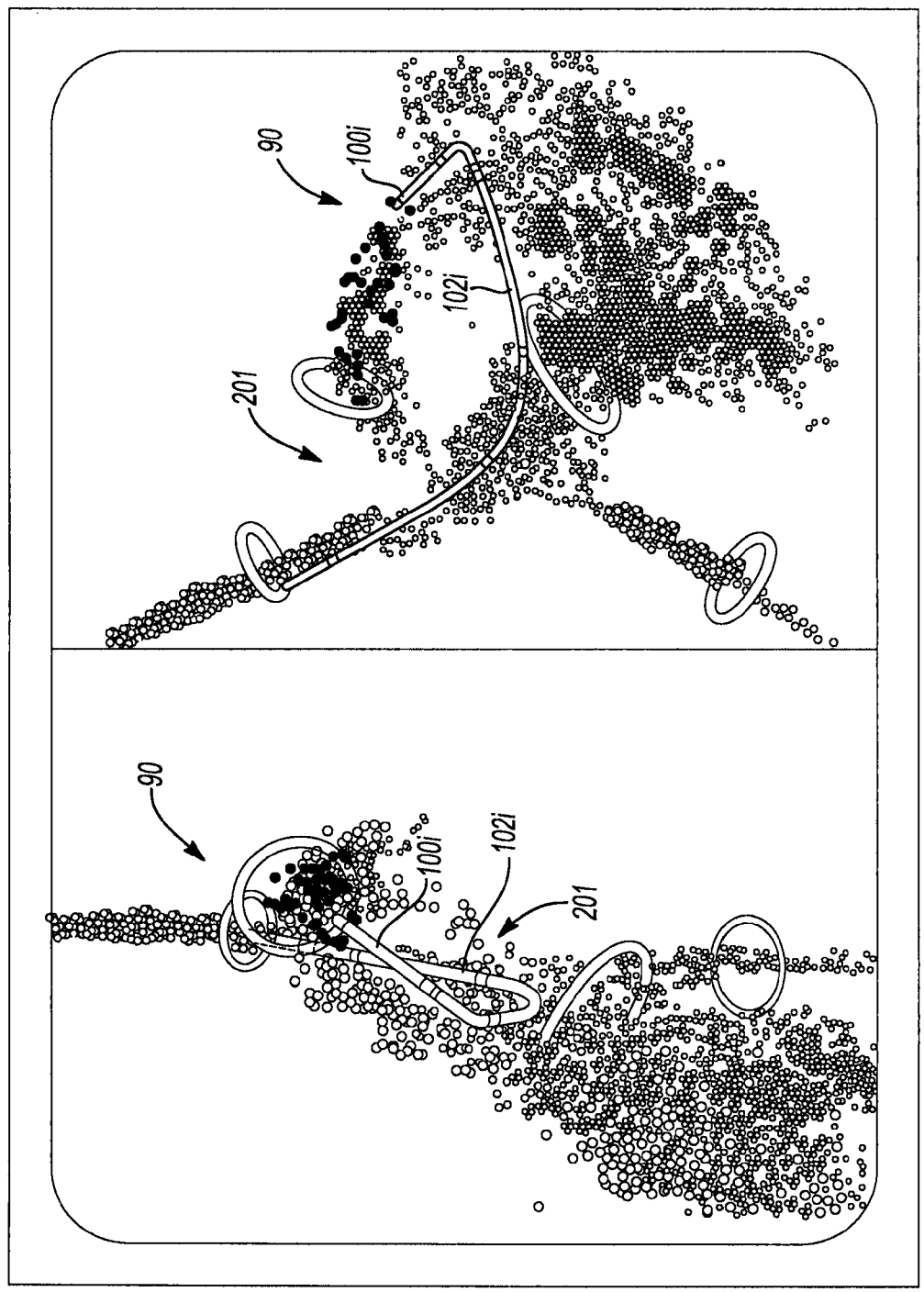

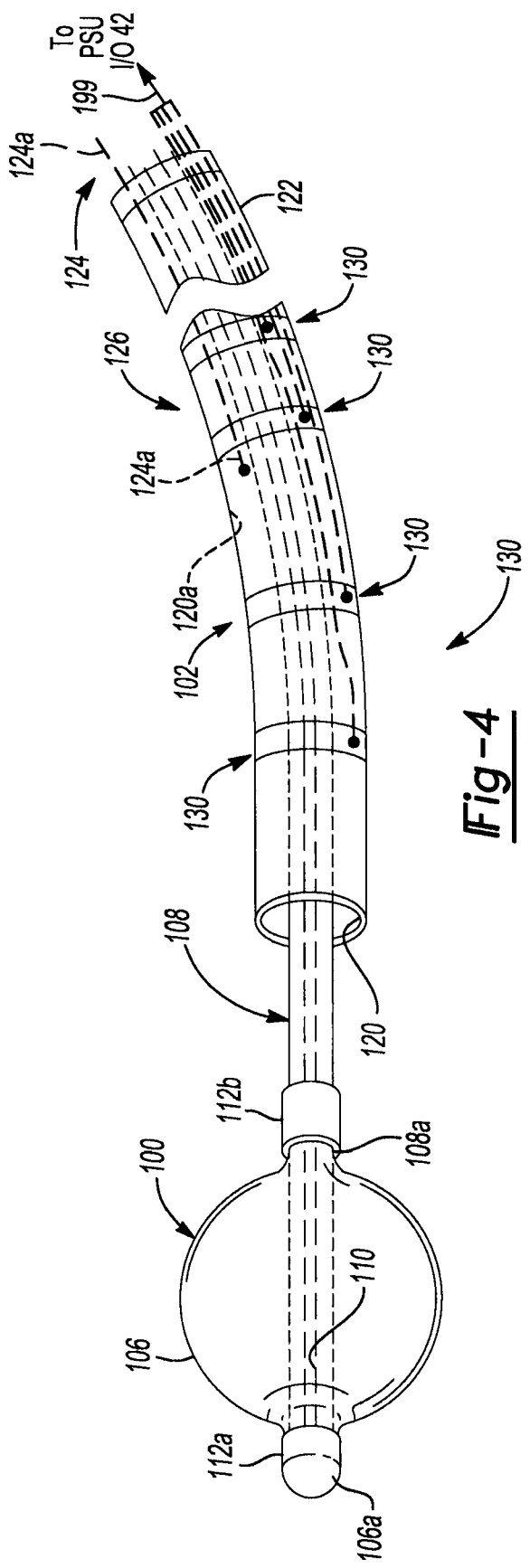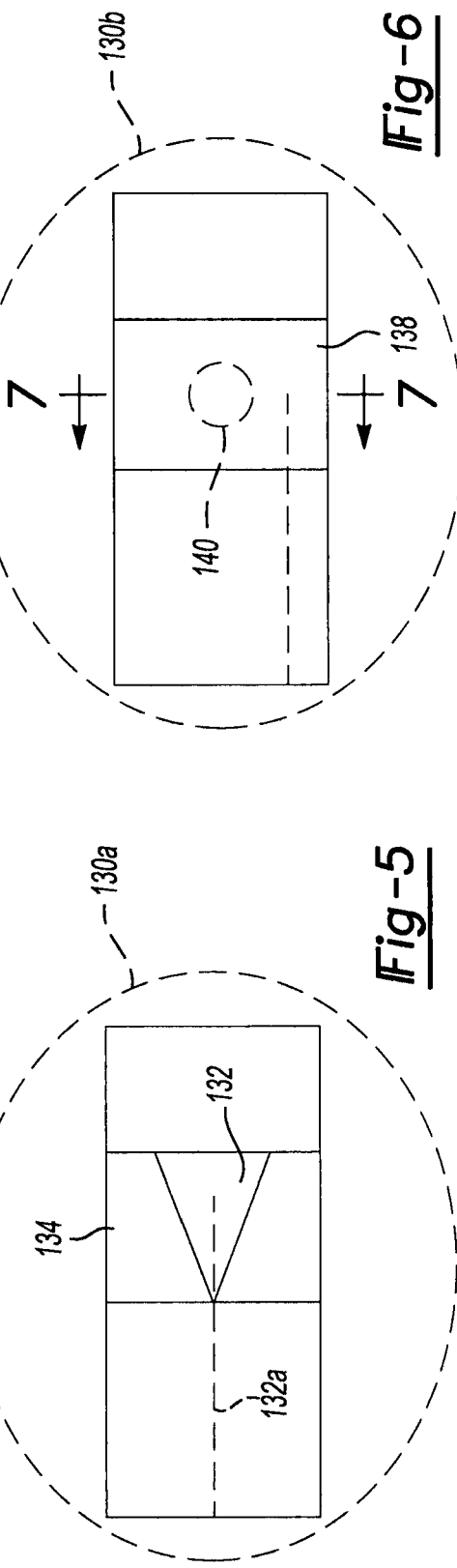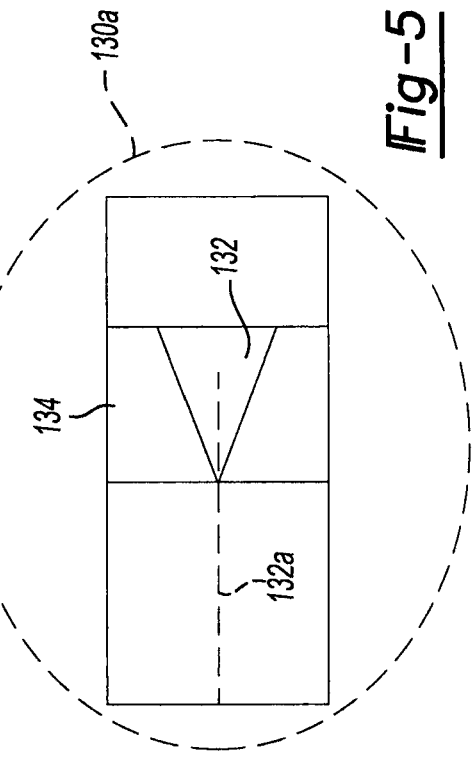

SYSTEM AND METHOD FOR DETERMINING SHEATH LOCATION

CROSS-REFERENCE TO RELATED APPLICATIONS

This application includes subject matter that relates to co-pending U.S. provisional application 61/046,298, filed on Apr. 18, 2008; U.S. patent application Ser. No. 12/117,537, filed on May 8, 2008; U.S. patent application Ser. No. 12/117,549, filed on May 8, 2008; and U.S. patent application Ser. No. 12/421,364 and U.S. patent application Ser. No. 12/421,332, filed concurrently herewith. The entire disclosures of the above applications are incorporated herein by reference.

FIELD

The present disclosure relates generally to surgical navigation systems, and in particular to a system and method for determining a position or location of a sheath within an anatomy.

BACKGROUND

The statements in this section merely provide background information related to the present disclosure and may not constitute prior art.

The human anatomy includes many types of tissue that can either voluntarily or involuntarily, perform certain functions. However, after disease or injury, certain tissues may no longer operate within general anatomical norms. For example, after disease, injury, age, or combinations thereof, the heart muscle may begin to experience certain failures or deficiencies. Some of these failures or deficiencies can be corrected or treated with implantable medical devices (IMDs). These devices can include implantable pulse generator (IPG) devices, pacemakers, implantable cardioverter-defibrillator (ICD) devices, cardiac resynchronization therapy defibrillator devices, or combinations thereof.

One of the main portions of the IMD can include a lead that is directly connected to tissue to be affected by the IMD. The lead can include a tip portion that is directly connected to the anatomical tissue, such as a muscle bundle, and a lead body that connects to the device body or therapeutic driving device. It is generally known that the device body or case portion can be implanted in a selected portion of the anatomical structure, such as in a chest or abdominal wall, and the lead can be inserted through various venous portions so that the tip portion can be positioned at the selected position near or in the muscle group.

The IMDs are implantable devices that may require the use of imaging devices for implantation. The imaging devices can include fluoroscopes that expose a patient and a surgeon to ionizing radiation. In addition, the use of the imaging device can require time for acquiring image data and understanding the images from the image data.

SUMMARY

A position sensing unit (PSU) system is operable to map and illustrate mapped and saved points. The system can determine the location of an electrode by generating a voltage in a patient and calculating an impedance at the electrode. The calculated impedance is used to determine the position of the electrode as in a patient or other appropriate conducting medium.

The saved points may be used to create a map determined with the electrode that can be used to determine a location of a later positioned electrode. The electrode positioned in the anatomy can include a navigation catheter, pacing lead, etc. The map generated with the PSU can be used to guide or navigate a lead to a selected location without external imaging devices. Generally, the navigation catheter or pacing lead can be inserted into the anatomy, via a sheath.

A system for determining a location of an instrument within an anatomy is provided. The system can include a first instrument navigable within the anatomy, which can define at least one lumen. The first instrument can include a proximal end and a distal end. The system can further include a second instrument, which can be received through the at least one lumen and navigable within the anatomy relative to the first instrument. The system can include at least one electrode, which can be coupled to the distal end of the first instrument. The at least one electrode can be responsive to electrical activity to generate at least one signal. The system can include a sensing unit, which can be in contact with the anatomy to sense electrical activity within the anatomy at a location near the instrument. The sensing unit can be in communication with the at least one electrode to receive the at least one signal. The system can further include a control module that can determine, based on the sensed electrical activity and the at least one signal, the location of the first instrument. The at least one electrode can be slittable so that the first instrument can be removed from about the second instrument.

In one example, a system for determining a location of an instrument within an anatomy can be provided. The system can include a first electrode patch in contact with the anatomy. The system can further include a second electrode patch in contact with the anatomy and spaced apart from the first electrode patch. The system can include a first instrument, which can be navigable within the anatomy relative to the first electrode patch and the second electrode patch. The first instrument can define at least one lumen, and can include a distal end. The system can further include a second instrument, which can be received through the at least one lumen. The second instrument can be navigable within the anatomy relative to the first instrument, the first electrode patch and the second electrode patch. The system can include at least one electrode coupled to the distal end of the first instrument. The at least one electrode can be responsive to electrical activity to generate at least one signal. The system can further include a sensing unit, which can be in communication with the first electrode patch and the second electrode patch to generate voltages between the first electrode patch and the second electrode patch. The sensing unit can also be in communication with the at least one electrode of the first instrument to receive the at least one signal. The sensing unit can determine at least one impedance of the at least one electrode of the first instrument based on the at least one signal. The system can also include a control module that can determine, based on the at least one impedance of the at least one electrode of the first instrument, the location of the first instrument within the anatomy.

According to various examples, a method can be provided for determining a location of an instrument within an anatomy. The method can include providing a first instrument that includes at least one lumen. The method can include inserting a second instrument into the at least one lumen. The method can further include inserting the second instrument and at least a portion of the first instrument into the anatomy. The method can also include sensing electrical activity within the anatomy near the portion of the first instrument. The method can include determining, based on the sensed electrical activity, the location of the first instrument. The method can also include slitting the at least one electrode to remove the first instrument from the anatomy without removing the second instrument.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIG. 3 is a schematic environmental view of a display device displaying exemplary data generated by the navigation system of FIG. 1;

FIG. 4 is a detail view of an exemplary navigation catheter and exemplary sheath for use with the navigation system of FIG. 1;

FIG. 5 is a detail side view of an exemplary electrode for use with the sheath of FIG. 4;

FIG. 6 is a detail side view of an exemplary electrode for use with the sheath of FIG. 4;

DETAILED DESCRIPTION

Figure 1:
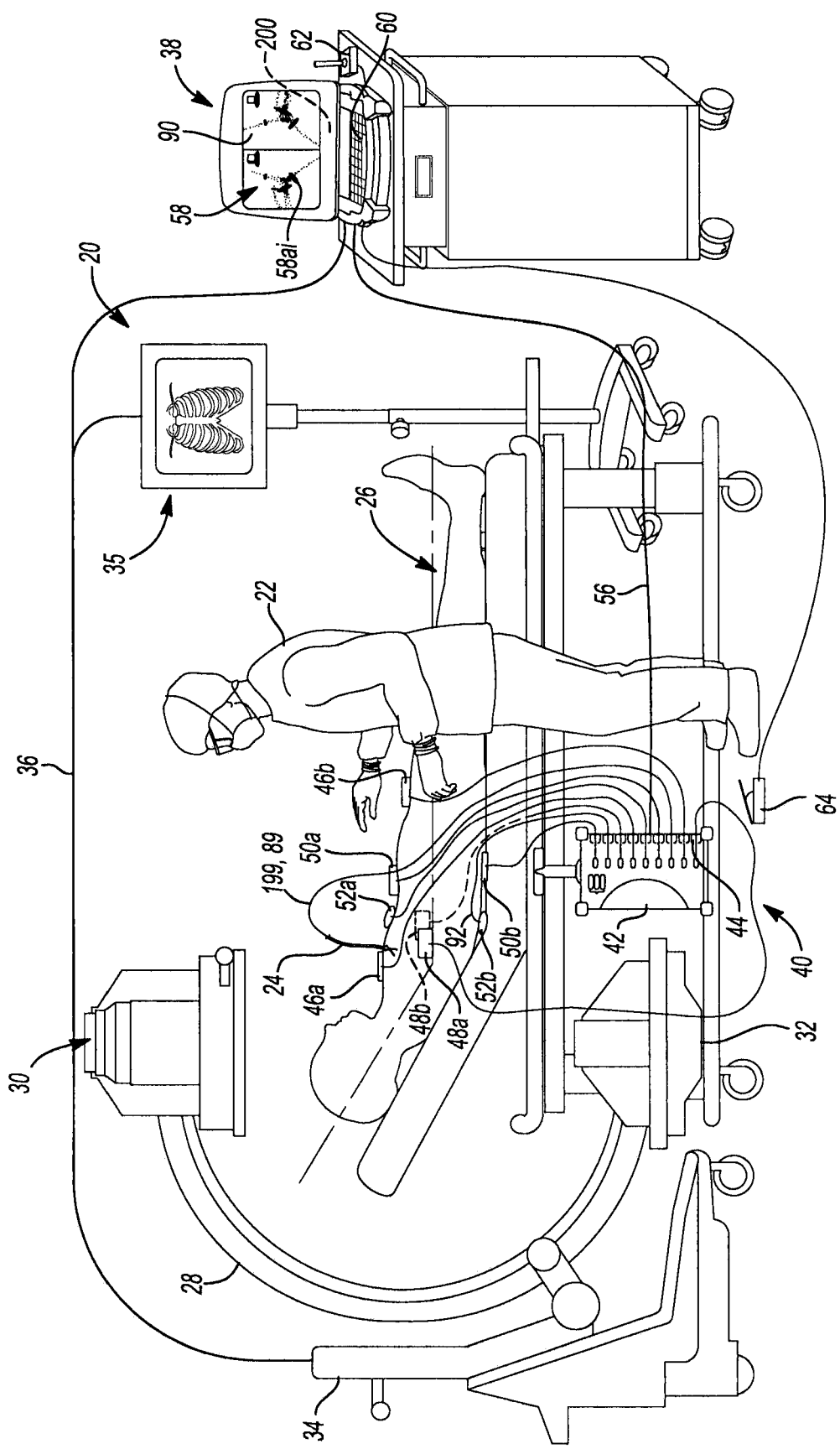
FIG. 1 is an environmental view of a mapping or navigation system.

The following description is merely exemplary in nature and is not intended to limit the present disclosure, application, or uses. It should be understood that throughout the drawings, corresponding reference numerals indicate like or corresponding parts and features. As indicated above, the present teachings are directed towards providing a system and method for determining a location or position of a sheath. It should be noted, however, that the present teachings could be applicable to any appropriate procedure in which it is desirable to determine a position of an instrument within an anatomy. Further, as used herein, the term "module" can refer to an application specific integrated circuit (ASIC), an electronic circuit, a processor (shared, dedicated, or group) and memory that executes one or more software or firmware programs, a combinational logic circuit, and/or other suitable hardware or software, firmware programs or components that provide the described functionality. Therefore, it will be understood that the following discussions are not intended to limit the scope of the appended claims.

As discussed herein, a navigation system, such as the navigation system 20 illustrated in FIG. 1, can be used to navigate a procedure relative to a patient 26. As discussed in detail herein, various instruments can be moved relative to the patient 26 and tracked relative to the patient 26. Although an image-guided system can include acquiring image data of the patient 26, such as with an imaging device 28, such an imaging device is not required, as discussed herein. A portion of the patients' anatomy can be mapped by identifying a plurality of points within the patient by determining a relative location of an instrument. The plurality of points can be illustrated individually, sequentially, or a surface can be illustrated over or without the plurality of points to illustrate or identify a portion of the anatomy of the patient 26. Once the map has been created of the patient or a portion of the patient, either with or without a surface rendered relative to the individual points, a procedure can be guided or navigated using the map or point data. The point or map data 90 can be generated without any additional imaging information, such as image data that can be acquired with a fluoroscopic system, MRI Imaging System, computed tomography (CT) Imaging System, or other imaging systems.

With reference to FIG. 1, the exemplary mapping or navigation system 20 is illustrated. The navigation system 20 can be operated by the user 22 with an instrument 24 to map a selected space, such as a portion of the patient 26. The instrument 24 can also be navigated relative to the patient 26. The instrument 24 can be moved relative to the patient 26 for various procedures, including lead placement relative to the heart, mapping of the heart, mapping of a selected organ of the patient 26, or guiding or navigating the instrument 24 relative to any appropriate portion of the patient 26. Generally, the instrument 24 can comprise any suitable instrument for use with an anatomy, such as a catheter, balloon catheter, mapping catheter, basket catheter, guide wire, arthroscopic system, cardiac lead, orthopedic implant, spinal implant, deep-brain stimulator (DBS) probe, microelectrode recorder probe, macroelectrode stimulation probe, etc.

The navigation system 20 can include various components, such as an optional imaging device 28. The optional imaging device 28 can include a fluoroscope, such as a fluoroscope configured as a C-arm. The C-arm fluoroscope can include an imaging section 30 and an x-ray emitting section 32. The imaging device 28 can be controlled by a controller 34. Images acquired with the imaging device 28 can be displayed on a display 35 that is associated with the imaging device 28, or could be displayed on the display 58. Thus, it will be understood, that a separate display 35 is not required. In addition, if the imaging device 28 is an x-ray imaging device any radio-opaque portions will appear as a part of the image when viewed, including the instrument 24.

The controller 34 can control the imaging device 28 and can store images generated with the imaging device 28 or transmit data or receive instructions via a data transmission or communication line 36 to or from a processor and/or memory, such as one that may be included in a workstation 38. While the optional imaging device 28 illustrated here is a fluoroscopic c-arm other imaging devices, such as CT, MRI, ultrasound, etc., can also be employed. Moreover, it will be understood that the communication line 36 can be any appropriate communication line such as a wired communication line, a wireless communication system, or any other data transfer mechanism.

Figure 2:
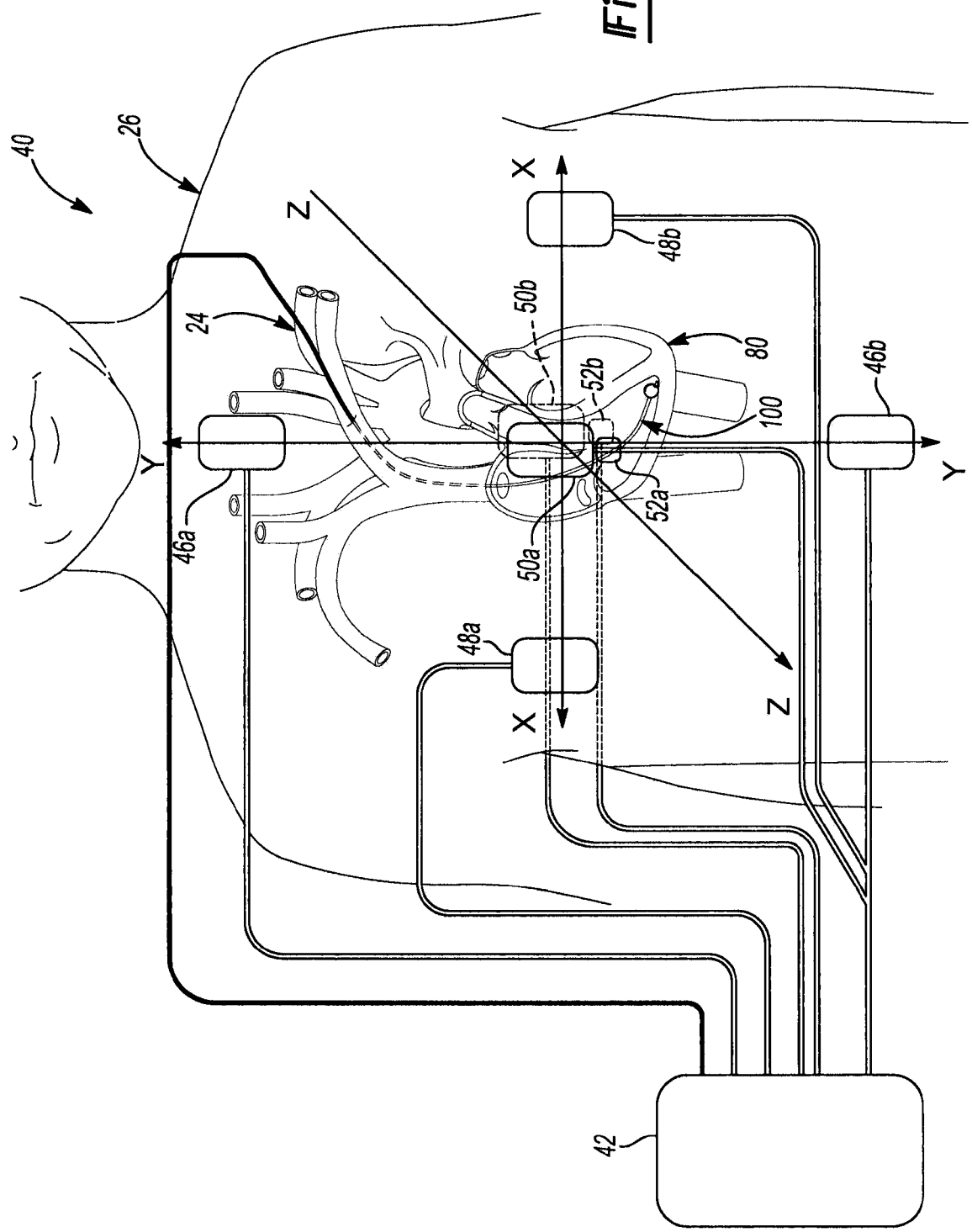
FIG. 2 is a detailed view of a position sensing unit, according to various embodiments.

The navigation system 20 can further include a Position Sensing Unit (PSU) 40, as illustrated in FIG. 2. The PSU 40 can include an impedance or Electrical Potential (EP) system. The PSU 40 can be the LocaLisa® Intracardiac Navigation System, which was commercially available from Medtronic, Inc. of Minneapolis, Minn., USA. The PSU 40 can also be that disclosed in U.S. Pat. Nos. 5,697,377 or 5,983,126 to Wittkampf, incorporated herein by reference. The PSU 40 can include a control or driving unit 42 that includes one or more input or output connectors 44 to interconnect with one or more current conducting electrode or drive patches, which can be generally identified by reference numerals 46, 48 and 50. The electrode or drive patches 46, 48, 50 can be connected directly to the patient 26. As an example, the LocaLisa® device can be used to generate the current in the patient 26. In one example, the drive patches 46, 48, 50 can include three drive patches 46, 48, 50 which can create three substantially orthogonal voltage or current axes x, y, z within the patient 26.

In this regard, for example, a first y-axis drive patch 46a and a second y-axis drive patch 46b can be interconnected with the patient 26 to form a y-axis (such as an axis that is generally superior-inferior of a patient) with a conductive path such that the conducted current establishes a voltage potential gradient substantially along this axis and between the drive patches 46a and 46b. A related y-axis current flows from the first y-axis drive patch 46a to the second y-axis drive patch 46b substantially along the y-axis. Likewise, a first x-axis drive patch 48a and a second x-axis drive patch 48b can be connected with the patient 26 to create an x-axis (such as an axis that is generally medial-lateral of a patient) with a voltage gradient substantially along the x-axis between the drive patches 48a and 48b and a corresponding x-axis current. Finally, a first z-axis drive patch 50a and a second z-axis drive patch 50b can be connected with a patient 26 to create a z-axis (such as an axis that is generally anterior-posterior of a patient) with a voltage potential gradient substantially along the z-axis between the drive patches 50a and 50b with a corresponding z-axis current.

The three axes x, y, z are generally formed to have an origin or area of interest that the common intersection or origin of each of the axes x, y, z. Accordingly, the drive patches 46, 48, 50 can be positioned on the patient 26 to achieve the selected placement of the axes x, y, z relative to the patient 26. Each of the drive patches 46a-50b can be interconnected with the PSU input/output (I/O) box 42, via a wire connection or other appropriate connection at the connectors 44.

The current applied between the related patches generate a small current, (about 1 microampere to about 100 milliamperes), in the patient along the axis between the respective patch pairs. The induced current can be of a different frequency for each of the related patch pairs to allow for distinguishing which axis x, y, z is being measured. The current induced in the patient 26 will generate a voltage gradient across different portions, such as a heart 80, that can be measured with an electrode, as discussed in further detail herein.

The sensed voltage can be used to identify a position along an axis (whereby each axis can be identified by the particular frequency of the current being measured) to generally determine a position of an electrode along each of the three axes x, y, z. Although a voltage can be sensed, an impedance can also be calculated or measured to determine a location in a similar manner. It will be understood, that a sensing of voltage will not eliminate other possible measurements for position determination, unless specifically indicated. As discussed further herein, the position of the electrode with respect to each of the three axes x, y, z can be used as map data 90 to be illustrated on the display 58. Electrodes within the patient 26 and reference electrode patches 52 are interconnected with the PSU I/O box 42 such that the signals are processed by high impedance circuitry so as to not load and distort the sensed signals.

In addition, one or more electrode or reference patches or reference electrode patches 52 can be interconnected with the patient 26 for reference of guiding or mapping with the instrument 24 relative to the patient 26. The reference electrode patches 52 can include a first reference electrode patch 52a and a second reference electrode patch 52b. The placement of the reference electrode patches 52a, 52b can be any appropriate position on the patient 26. For example, the first reference electrode patch 52a can be positioned substantially over the xiphoid process on the skin of the patient 26 directly exterior to the xiphoid process of the patient 26. The second reference electrode patch 52b can be positioned substantially directly across from the first reference electrode patch 52a on a dorsal surface of the patient 26. By positioning the reference electrode patch 52a at this location, the reference electrode patch 52a has relatively little motion with respect to the heart. The placement of the reference electrode patches 52a,b at these locations, can enable respiration of the patient 26 to be monitored by measuring the relative voltage or impedance difference between the two reference electrode patches 52a, 52b using the PSU 40.

In addition to reference electrode patches 52a, 52b being positioned on or near a xiphoid process of a patient, additional various reference patches or reference electrode patches can be positioned at other locations on the patient 26. Greater detail regarding the placement of reference patches or reference electrode patches can be found in U.S. Ser. No. 12/421,332 and U.S. Ser. No. 12/421,364, filed concurrently herewith, and incorporated herein by reference.

With reference to FIG. 1, the PSU I/O box 42 can be interconnected with the workstation 38, via a connection or data transfer system 56. The data transfer system 56 can include a wire transmission, wireless transmission, or any appropriate transmission. The data transfer system 56 can transmit signals 92, which can be analog or digital signals, regarding voltages sensed by the reference electrode patches 52a, 52b and signals 199, which can be analog or digital signals, regarding voltages sensed by electrodes on the instrument 24, as will be discussed herein. The workstation 38 can use the signals 92, 199 to determine a relative location of the instrument 24 and to display the determined relative location on the display 58 as instrument position data 201 (FIG. 3).

With continuing reference to FIG. 1, the display 58 can be integral with or separate from the workstation 38. In addition, various interconnected or cooperating processors and/or memory can be provided to process various information, each may be a part of the workstation 38 or separate therefrom. In one example, the workstation 38 can include one or more processors and one or more data storage devices. As can be appreciated, the processors can comprise one or more processing elements capable of implementing a control module 200. At least one of the data storage devices can store one or more instructions contained in a control system associated with the control module 200. In one example, the data storage device can be at least one of random access memory (RAM), read only memory (ROM), a cache, a stack, or the like, which may temporarily or permanently store electronic data. As will be discussed, the control module 200 can receive the signals 92 from the reference electrode patches 52 and the signals 199 from the instrument 24 to determine the position of the instrument 24, and display the determined positions or other data on the display 58.

The navigation system 20 can further include user input or data input devices such as a keyboard 60, a joystick 62, or a foot pedal 64. Each of the input devices, 60-64 can be interconnected with the workstation 38 or appropriate systems for inputting information or data into the workstation 38. This information or data can include identifying appropriate information, as discussed further herein, such as various components, or anatomic regions.

The instrument 24 can include an electrode, as discussed further herein, which is able to sense the voltage generated within the patient 26 due to the drive patches 46a-50b positioned on the patient 26. The sensed voltage can be used to calculate an impedance of the tissue in the patient 26 based upon the voltage potential gradient generated between the respective pairs of drive patches 46a-50b and the corresponding current. Generally, the current is carried due to an electrolyte in the patient 26, such as blood, interstitial fluid, etc. within a heart 80 and body of the patient 26. The calculated impedance or sensed voltage can be used to determine a location of the electrode of the instrument 24 relative to a selected reference, such as reference electrode patch 52a or 52b.

With reference to FIG. 4, according to various embodiments, one or more instruments 24 can be used with the PSU 40, such as a mapping or navigation catheter 100, which can be passed through a deflectable sheath 102. As the navigation catheter 100 can comprise any suitable navigation catheter 100 known in the art, such as a Swan-Ganz Balloon Catheter System sold by Edwards Lifesciences, the navigation catheter 100 will not be discussed in great detail herein. Briefly, however, the navigation catheter 100 can include various portions, such as an expandable, inflatable or balloon portion 106, a catheter 108 that can define a lumen 110 and one or more electrodes 112.

The balloon portion 106 can be formed at a distal end 114 of the catheter 108. The balloon portion 106, when inflated, can act as a stop when the navigation catheter 100 is being moved through the heart 80 or other anatomical portion. The balloon portion 106 can be inflated or deflated as selected by the user 22. For example, the inflation of the balloon portion 106 can be performed in any appropriate manner such as directing a fluid, such as a liquid or gas, through the lumen 110.

The electrodes 112 can include a first or tip electrode 112a and a second or ring electrode 112b. The tip electrode 112a can be coupled to a distal end 106a of the catheter 108, while the ring electrode 112b can be provided on a proximal end 108a of the balloon portion 106. The electrodes 112 can be used to sense voltages within the patient 26 when the navigation catheter 100 is positioned within the patient 26 and the drive patches 46-50 are active or being driven. In this regard, with reference to FIG. 1, the electrodes 112 can sense voltages produced within the patient 26 by the drive patches 46-50, which can be transmitted to the PSU 40 as a signal 89. Various conductors can be used to transfer the sensed voltages from the electrodes 112 to the PSU I/O box 42. From the sensed voltages, the PSU 40 can calculate impedances to determine a position of the navigation catheter 100 within the anatomy. With reference to FIG. 3, the position of the navigation catheter 100 can be displayed as an icon 100i on the display 58. Note that the icon 100i can be superimposed on the map data 90 illustrated on the display 58. The navigation catheter 100 can be moved relative to the patient 26 in any appropriate manner, such as with the sheath 102.

With further reference to FIG. 4, the sheath 102 can define a throughbore or lumen 120, which can receive the navigation catheter 100. The sheath 102 can be used by the user 22 to direct or guide the navigation catheter 100 within the anatomy, and can also be used to direct or guide a lead for use with an IMD within the anatomy. The sheath 102 can be composed of a suitable deflectable material, such as a biocompatible polymer, and can include a proximal end 122, a steering mechanism 124 and a distal end 126. The proximal end 122 of the sheath 102 can generally extend outside of the anatomy, and can be configured to enable the user 22 to manipulate and direct the sheath 102 within the anatomy.

The steering mechanism 124, in one example, can comprise a pull wire 124a, which can be coupled to an interior surface 120a of the lumen 120 near the distal end 126. In one example, the pull wire 124a could be coupled to an electrode 130 and could serve as a conductor for the electrode 130. As is generally known, the pull wire 124a can be manipulated or pulled by the user to curve or bend the distal end 126 of the sheath 102. This can enable the distal end 126 of the sheath 102 to navigate the curvatures within the anatomy and to direct the exit of an instrument from the lumen 120.

With reference to FIG. 4, the distal end 126 of the sheath 102 can include one or more electrodes 130. In one example, the sheath 102 can include two electrodes 130, and in one example, the sheath 102 can include four electrodes 130. The use of at least two electrodes 130 can enable the PSU 40 to determine a position of the distal end 126 of the sheath 102 based on voltages sensed by the electrodes 130. In this regard, the electrodes 130 can be used to sense voltages within the patient 26 when the sheath 102 is positioned within the patient 26 and the drive patches 46-50 are active or being driven. The electrodes 130 can sense voltages produced within the patient 26 by the drive patches 46-50, and from the sensed voltages impedances can be calculated by the PSU 40 to determine a position of the sheath 102. Various conductors can be used to transfer the sensed voltages from the electrodes 130 to the PSU I/O box 42. With reference to FIG. 3, the position of the distal end 126 of the sheath 102 can be displayed on the display 58 as an icon 102i. Note that the icon 102i can be superimposed on the map data 90 illustrated on the display 58.

The sheath 102 can be used to insert various instruments into the anatomy, and in one example, can be used to guide a lead into the anatomy. Due to the size of a connector on the proximal end of the lead, it can be desirable to cut or slit the sheath 102 after the lead has been properly positioned in the anatomy. In order to slit the sheath 102, the electrodes 130 can be slittable.

In one example, with reference to FIG. 5, at least one of the electrodes 130 can comprise an electrode 130a, which can comprise a metal portion, such as a metal electrode 132, which can be coupled to a conductive polymer band 134. The metal electrode 132 can have any desired shape, but can generally be shaped and sized such that the metal electrode 132 does not extend completely around or about the circumference of the sheath 102. For example, the metal electrode 132 can comprise a triangular shape, which can be positioned to guide a cutting tool to the side of the metal electrode 132, but the metal electrode 132 could comprise any suitable shape, such as a trapezoid, rectangle, square, oval, diamond, etc. The metal electrode 132 can be coupled to the PSU 40 via a suitable connector 132a. It should be noted that the connector 132a can also comprise the pull wire 124a, if desired. The metal band 136 can be coupled to and in communication with the conductive polymer band 134.

The conductive polymer band 134 can be coupled to the metal electrode 132 such that the electrode 130 can circumscribe the sheath 102. Thus, the size of the metal electrode 132 can influence the size of the polymer band 134. In one example, the metal electrode 132 can be embedded in the polymer band 134, however, it should be understood that the metal electrode 132 can be coupled adjacent to and not embedded within the polymer band 134. The polymer band 134 can be composed of any suitable conductive polymeric material, such as a silicon-based conductive polymeric material, and can cooperate with the metal electrode 132 to sense a voltage within the patient 26 uniformly about the circumference of the sheath 102.

Figure 7:
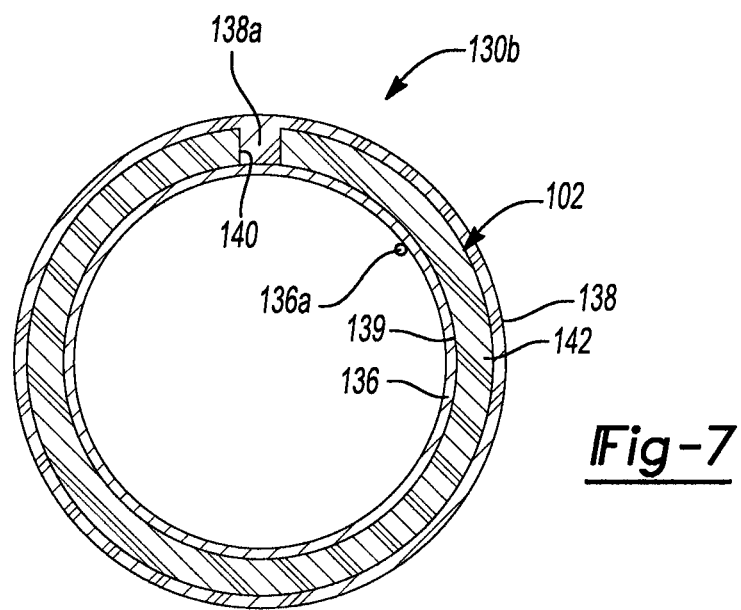
FIG. 7 is a cross-sectional schematic illustration of the electrode of FIG. 6, taken along line 7-7 in FIG. 6.

In one of various examples, with reference to FIGS. 6 and 7, at least one of the electrodes 130 on the sheath 102 can comprise an electrode 130b, which can include a metal portion, such as a metal band 136 and a conductive polymer band 138. It should be noted that the electrodes 130 on the sheath 102 can comprise any desired combinations of the electrodes 130a and 130b. The metal band 136 can in one example comprise a gold (Au) metal band, however, the metal band 136 can comprise any conductive metal or metal alloy that can be easily slit with a cutting device. The metal band 136, in one example, can be positioned within the sheath 102, such that the metal band 136 is adjacent to an interior surface 139 of the sheath 102. The metal band 136 can be coupled to the PSU 40 via a suitable connector 136a. It should be noted that the connector 136a can also comprise the pull wire 124a, if desired. The metal band 136 can also be coupled to and in communication with the conductive polymer band 138 via a bore 140 defined through the sheath 102.

In this regard, with reference to FIG. 7, the conductive polymer band 138 can be formed about the circumference of the sheath 102, and generally, can be formed about an exterior surface 142 of the sheath 102 at about the same location as the metal band 136, such that the metal band 136 and conductive polymer band 138 are concentric about the sheath 102. The conductive polymer band 138 can be formed over the bore 140, so that during the forming of the conductive polymer band 138, at least a portion 138a of the conductive polymer can flow through the bore 140 to contact the metal band 136. The portion 138a of the conductive polymer within the bore 140 can enable electrical communication between the metal band 136 and the conductive polymer band 138. The conductive polymer band 138 can comprise any suitable conductive polymeric material, such as a silicon-based conductive polymeric material, however any suitable conductive polymeric material could be employed.

Figure 8:
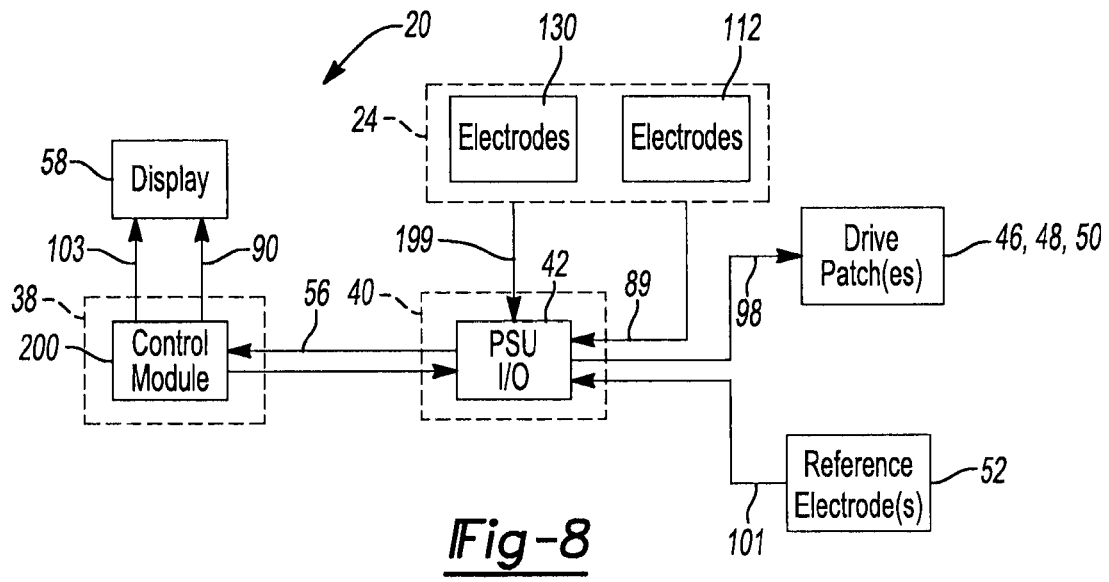
FIG. 8 is a simplified block diagram illustrating a navigation system for sheath detection.

With reference to FIG. 4, the electrodes 130 can sense voltages produced within the patient 26 by the drive patches 46-50, which can be output as a signal 199, and from the sensed voltages impedances can be calculated by the PSU 40 to determine a position of the sheath 102. With reference to FIG. 8, a simplified block diagram schematically illustrates an exemplary navigation system 20 for implementing the control module 200. The navigation system 20 can include the instrument 24, which in one example can comprise the navigation catheter 100 having the electrodes 112, and the sheath 102 having the electrodes 130. The navigation system 20 can also comprise the drive patches 46, 48, 50, the reference electrodes 52, the PSU 40, which can include the PSU I/O box 42, the display 58 and the workstation 38, which can implement the control module 200.

In one example, the PSU 40, via the PSU I/O box 42, can transmit a voltage 98 to the drive patches 46, which can create voltages in the patient 26. The electrodes 130 of the sheath 102 can transmit a signal 199 to the PSU I/O box 42, which can comprise the voltages sensed by the electrodes 130. Based on the voltages sensed by the electrodes 130, the control module 200 can determine a position of the sheath 102 within the anatomy. The electrodes 112 of the navigation catheter 100 can sense the voltages within the patient 26, and can transmit this data as the signal 89 to the PSU I/O box 42. Based on the sensed voltages, the PSU 40 can determine a position or location of the navigation catheter 100 within the anatomy.

The reference electrodes 52 can sense the voltages generated by the drive patches 46, 48, 50, and can transmit these sensed voltages as a signal 101 to the PSU I/O box 42. The signals 89, 199, 101 received by the PSU I/O box 42 can be transmitted to the workstation 38 as the signal 56, which can be received as input by the control module 200. Based on the data in the signal 56, the control module 200 can determine the position of the sheath 102 relative to the navigation catheter 100, and can output this data as instrument position data 201 for the display 58. The instrument position data 201 can comprise the icons 100i, 102i, which can indicate the position of the navigation catheter 100 and sheath 102 within the anatomy. The control module 200 can also output the map data 90 to the display 58. The instrument position data 201 can be superimposed on the map data 90, if desired.

Figure 9:
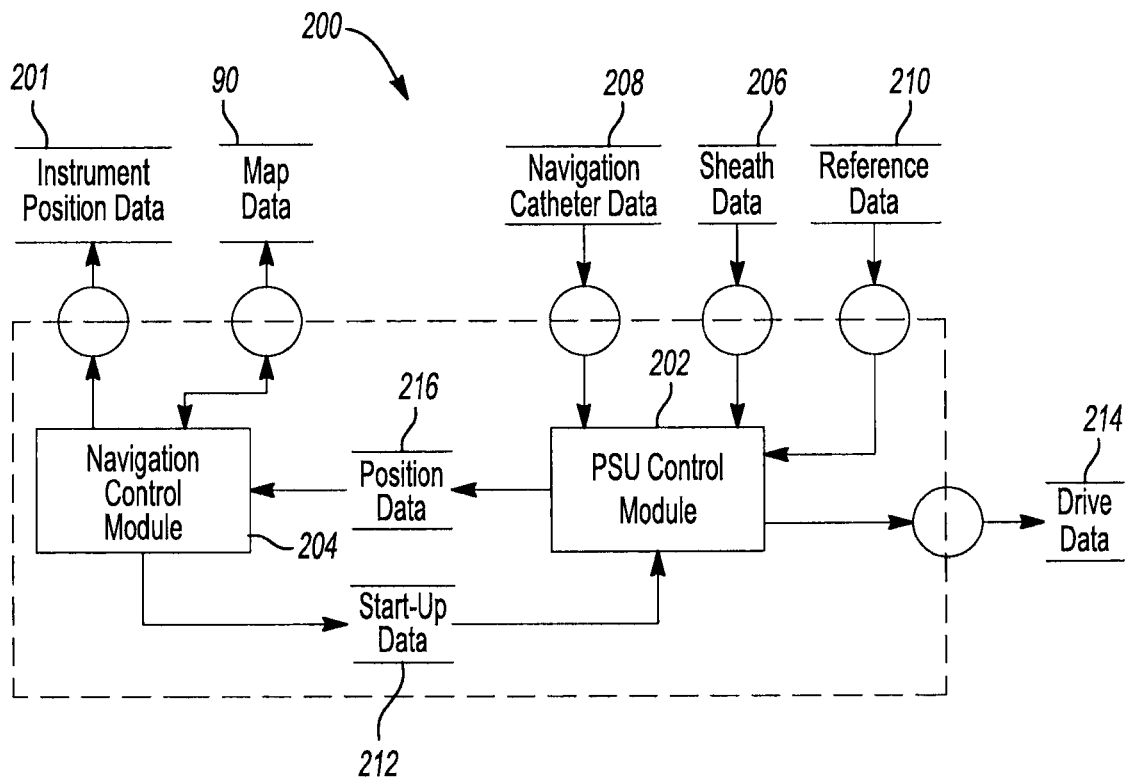
FIG. 9 is a dataflow diagram that illustrates a control system performed by a control module associated with the navigation system of FIG. 8.

In this regard, with reference to FIG. 9, a dataflow diagram illustrates the control system that can be embedded within the control module 200. Various embodiments of the control system according to the present disclosure can include any number of sub-modules embedded within the control module 200. The sub-modules shown may be combined and/or further partitioned to similarly determine a position of the navigation catheter 100 and the sheath 102. In various embodiments, the control module 200 can include a PSU control module 202 and a navigation control module 204.

The PSU control module 202 can receive as input sheath data 206, navigation catheter data 208 and reference data 210. The sheath data 206 can comprise the voltages sensed by the electrodes 130 of the sheath 102 or the data provided by signal 199. The navigation catheter data 208 can comprise the voltages sensed by the electrodes 112 of the navigation catheter 100, which can comprise the data from the signal 89. The reference data 210 can comprise the voltages sensed by the reference electrode patches 52a, 52b, which can comprise the data from the signal 101. The PSU control module 202 can also receive start-up data 212 as input. The start-up data 212 can comprise a signal to activate the PSU 40.

Based on the start-up data 212, the PSU 40 can output drive data 214. The drive data 214 can comprise a signal, which can drive the drive patches 46, 48, 50. Based on the sheath data 206, the navigation catheter data 208 and the reference data 210, the PSU control module 202 can set position data 216 for the navigation control module 204. The position data 216 can comprise data indicative of the position of the sheath 102 within the anatomy, and the position of the navigation catheter 100 relative to the reference electrodes 52. The position of the sheath 102 can be determined based on the impedances of the electrodes 130 of the sheath 102, which can be determined from the voltages sensed by the electrodes 130 of the sheath 102.

The navigation control module 204 can receive as input the position data 216. Based on the position data 216, the navigation control module 204 can output the map data 90, and instrument position data 201. The instrument position data 201 can comprise the icon 100i, which can graphically represent the position of the navigation catheter 100 and/or the icon 102i, which can graphically represent the position of the sheath 102. The navigation control module 204 can also set the start-up data 212 for the PSU control module 202, based upon receipt of an input, such as a user input from one of the user input devices 60-64.

Figure 10:
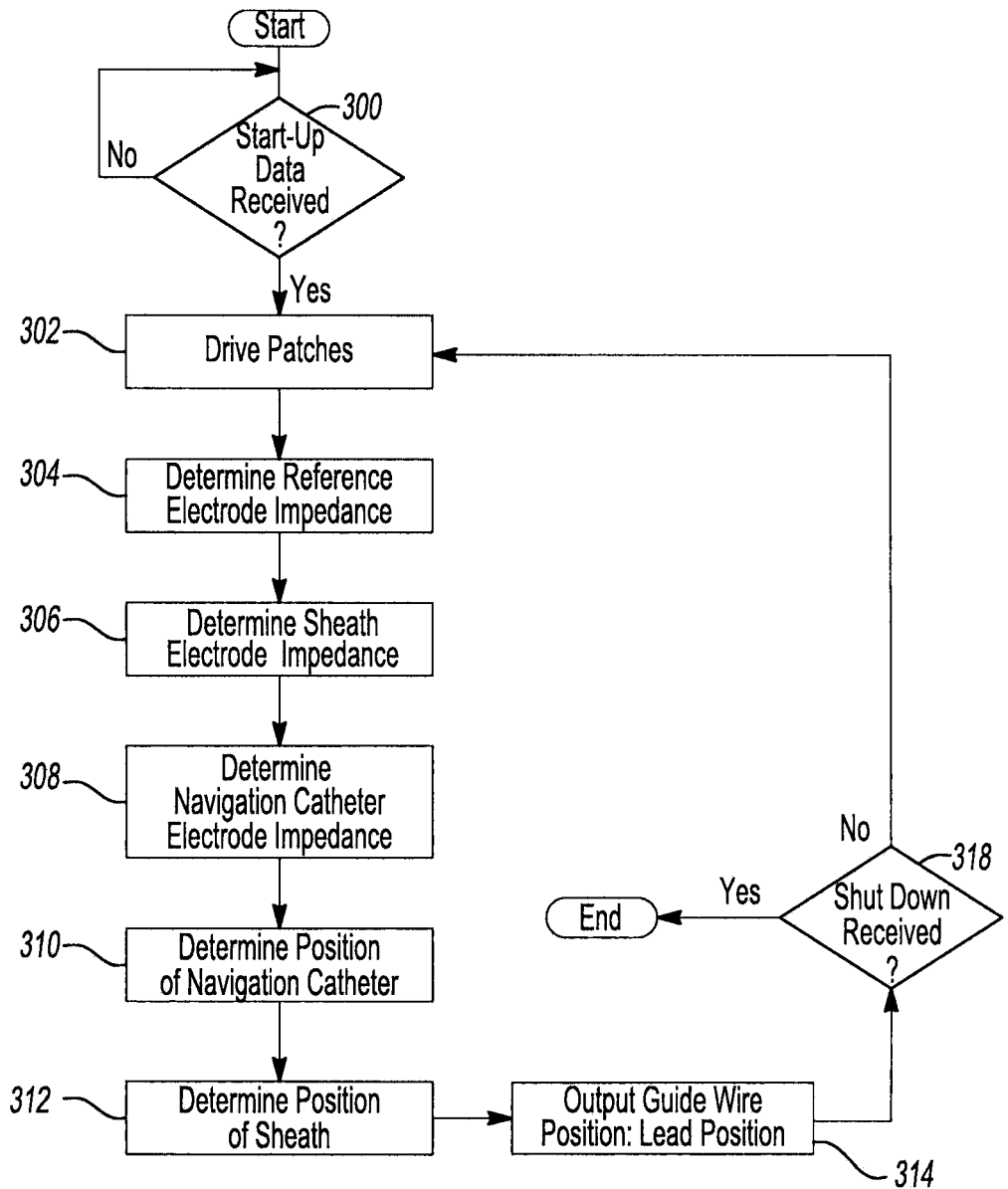
FIG. 10 is an exemplary flowchart diagram that illustrates one of various control methods performed by the control module of FIG. 9.

With reference now to FIG. 10, a flowchart diagram illustrates an exemplary method performed by the control module 200. At block 300, the method can determine if start-up data 212 has been received. If start-up data 212 has been received, then the method can go to block 302. Otherwise, the method can loop.

At block 302, the method can output the drive data 214 to drive the drive patches 46, 48, 50. At block 304, the method can determine impedances of the reference electrodes 52, based on the reference data 210. At block 306, the method can determine impedances of the electrodes 130 of the sheath 102, based on the sheath data 206. At block 308, the method can determine impedances of the electrodes 112 of the navigation catheter 100, based on the navigation catheter data 208. At block 310, the method can determine a position of the navigation catheter 100, given the impedances of the electrodes 112 of the navigation catheter 100 and the impedances of the reference electrodes 52.

At block 312, the method can determine a position of the sheath 102, given the impedances of the electrodes 130 of the sheath 102 and the impedances of the reference electrodes 52. At block 314, the method can output the map data 90 and the instrument position data 201 to the display 58. At block 318, the method can determine if a shut-down request was received. If a shut-down request was not received, then the method can go to block 302.

Thus, the navigation system 20 can provide a passive means for determining a location or position of the sheath 102 within the anatomy. In this regard, by sensing the impedances of the electrodes 130 of the sheath 102, the navigation system 20 can determine the position of the sheath 102 within the anatomy. This can enable the user 22 to know where the sheath 102 relative to other instruments in the anatomy, such as the navigation catheter 100. This can provide the user 22 with better situational awareness of the position of the sheath 102 relative to the navigation catheter 100, which can enable the user 22 to more effectively manipulate the navigation catheter 100 via the sheath 102. In addition, knowing the position of the sheath 102 within the anatomy may enable the user 22 to perform a mapping procedure faster.

While specific examples have been described in the specification and illustrated in the drawings, it will be understood by those of ordinary skill in the art that various changes may be made and equivalents may be substituted for elements thereof without departing from the scope of the present disclosure. Furthermore, the mixing and matching of features, elements and/or functions between various examples is expressly contemplated herein so that one of ordinary skill in the art would appreciate from this disclosure that features, elements and/or functions of one example may be incorporated into another example as appropriate, unless described otherwise, above. Moreover, many modifications may be made to adapt a particular situation or material to the teachings of the present disclosure without departing from the essential scope thereof. Therefore, it is intended that the present disclosure not be limited to the particular examples illustrated by the drawings and described in the specification as the best mode presently contemplated for carrying out this disclosure, but that the scope of the present disclosure will include any embodiments falling within the foregoing description.

For example, while the position of the sheath 102 has been described as being determined based on a sensed voltage of the electrodes 130, the sheath 102 may be constructed somewhat differently. In this regard, at least one tracking device, such as an electromagnetic coil, could be coupled at or near the distal end 126 of the sheath 102. Then, a suitable navigation system could be used to determine a position of the sheath 102, such as the StealthStation® AXIEM™ Electromagnetic Tracking System, commercially available from Medtronic, Inc. of Minneapolis, Minn., USA, or the navigation system described in commonly assigned U.S. Ser. No. 12/115,907, filed on May 6, 2008, which is incorporated herein by reference.

What is claimed is:

1. A system for determining a location of an instrument within an anatomy comprising:

a first instrument navigable within the anatomy that defines at least one lumen, and includes a proximal end and a distal end;
a second instrument received through the at least one lumen and navigable within the anatomy relative to the first instrument;
at least one electrode coupled to the distal end of the first instrument, wherein the at least one electrode is responsive to electrical activity to generate at least one signal, wherein the at least one electrode includes a first metal portion and a second polymer portion configured to be slit such that the at least one electrode is slittable from around the second instrument, wherein the first metal portion only partially surrounds the first instrument and the second polymer portion is coupled to the first metal portion;
a sensing unit to sense electrical activity within the anatomy at a location near the at least one electrode, the sensing unit in communication with the at least one electrode to receive the at least one signal;
a control module that determines, based on the sensed electrical activity and the at least one signal, the location of the first instrument.

2. The system of claim 1, further comprising:
a first drive patch adapted to be in contact with the anatomy; and
a second drive patch adapted to be in contact with the anatomy and spaced apart from the first drive patch, the first drive patch and the second drive patch positioned at or near the location.

3. The system of claim 2, further comprising:
a first reference patch adapted to be in contact with the anatomy and spaced apart from the first drive patch and the second drive patch; and
a second reference patch adapted to be in contact with the anatomy and spaced apart from the first drive patch, the second drive patch and the first reference patch, the first reference patch and the second reference patch adapted to be positioned at or near the location.

4. The system of claim 3, wherein the sensing unit generates a voltage between the first drive patch and the second drive patch and the sensed electrical activity comprises voltages sensed between the first reference patch and the second reference patch.

5. The system of claim 4, wherein the at least one electrode of the first instrument is responsive to the voltages between the first drive patch and the second drive patch, and the at least one signal from the at least one electrode comprises at least one voltage sensed by the at least one electrode.

6. The system of claim 5, wherein based on the sensed electrical activity between the first drive patch and the second drive patch, and the at least one signal from the at least one electrode, the control module determines at least one impedance of the at least one electrode of the first instrument.

7. The system of claim 6, wherein the control module determines a position of the second instrument relative to the anatomy based on the at least one impedance of the at least one electrode of the first instrument.

8. The system of claim 4, wherein the second instrument further comprises:
at least one second instrument electrode at a distal end, the at least one second instrument electrode responsive to the voltage to generate at least one second instrument signal that indicates at least one voltage sensed by the at least one second instrument electrode; and
wherein the sensing unit is in communication with the at least one second instrument electrode to receive the at least one second instrument electrode signal, and based on the sensed electrical activity and the at least one second instrument signal, the control module determines at least one impedance of the at least one second instrument electrode of the second instrument.

9. The system of claim 8, further comprising:
a display that displays the position of the first instrument relative to the second instrument;
wherein the control module determines a position of the first instrument relative to the anatomy based on the at least one impedance of the at least one second instrument electrode of the second instrument.

10. The system of claim 1, wherein the second instrument comprises a catheter, balloon catheter, mapping catheter, basket catheter, guide wire, arthroscopic system, cardiac lead, implant or combinations thereof.

11. The system of claim 1, which the first portion and the second portion together completely surround the first instrument.

12. A system for determining a location of an instrument within an anatomy comprising:
a first electrode patch adapted to be in contact with the anatomy;
a second electrode patch adapted to be in contact with the anatomy and spaced apart from the first electrode patch;
a first instrument that is navigable within the anatomy relative to the first electrode patch and the second electrode patch, wherein the first instrument has an outer wall that defines at least one lumen and includes a distal end;
a second instrument received through the at least one lumen and moveable relative to the first instrument and wherein the second instrument is navigable within the anatomy with a second instrument electrode relative to the first instrument, the first electrode patch, and the second electrode patch;
at least one first instrument electrode coupled to the distal end of the first instrument, wherein the at least one first instrument electrode and the second instrument electrode are responsive to electrical activity to each generate at least one signal;
a sensing unit in communication with the first electrode patch and the second electrode patch to generate voltage between the first electrode patch and the second electrode patch, the sensing unit in communication with the at least one first instrument electrode of first instrument to receive the at least one signal and to determine at least one impedance of the at least one first instrument electrode of the first instrument based on the at least one signal; and a control module that determines, based on the at least one impedance of the at least one first instrument electrode of the first instrument, the location of the first instrument within the anatomy;
wherein the at least one first instrument electrode further comprises:
a metal portion that extends around a circumference of the first instrument on an inner surface; and
a polymeric band that extends around the circumference on an outer surface;
wherein the metal portion and the polymeric band are coupled through the wall of the first instrument.

13. The system of claim 12, wherein the at least one first instrument electrode further comprises:
the metal portion in communication with the sensing unit; and
the polymeric band extending from the metal portion.

14. The system of claim 13, wherein the metal portion comprises a metal electrode that does not circumscribe the circumference of the first instrument.

15. The system of claim 14, wherein the metal electrode has a shape adapted to direct a cutting instrument, the shape selected from the group comprising a triangle, diamond, trapezoid, oval, circle, rectangle and a polygon.

16. The system of claim 14, wherein the metal electrode has a shaped portion configured to position and direct a cutting tool to slit the metal electrode.

17. The system of claim 13, wherein the at least one first instrument electrode is able to be slit so as to no longer extend around the circumference of the first instrument so that the first instrument can be removed without removing the second instrument.

18. The system of claim 12, wherein the at least one first instrument electrode comprises:
the polymeric band in communication with the metal portion via a bore defined through the first instrument; and
a suitable connector coupling the metal portion to the sensing unit.

19. The system of claim 18, wherein the polymeric band is formed over the lumen of the first instrument so that during the forming of the polymeric band at least a portion of a conductive polymer comprising the polymeric band flows through the lumen to contact the metal portion.

20. The system of claim 12, wherein the first instrument defines a bore which receives a portion of the polymeric band to couple to and enable electrical communication between the metal portion and the polymeric band.

21. The system of claim 20, wherein the metal band portion is internally positioned relative to the polymeric band and both are concentric about a center point of the first instrument.

22. A method for determining a location of an instrument within an anatomy comprising:
providing a first instrument that includes at least one lumen and at least one electrode substantially circumscribing the at least one lumen, wherein the at least one electrode is configured to be slit;
inserting a second instrument into the at least one lumen;
inserting the second instrument and at least a portion of the first instrument into the anatomy;
evaluating the location of the first instrument based upon a sensed electrical activity within the anatomy of the at least one electrode substantially circumscribing the at least one lumen; and
slitting the at least one electrode to remove the first instrument from around the second instrument and the anatomy without removing the second instrument;
wherein slitting the at least one electrode includes slitting a polymeric portion that is coupled to a metal portion, wherein the metal portion only partially surrounds the first instrument.

23. The method of claim 22, further comprising:
coupling a first drive patch to the anatomy;
coupling a second drive patch to the anatomy at a location spaced apart from the first drive patch; and
generating voltages in the first drive patch and the second drive patch.

24. The method of claim 23, further comprising:
sensing at least one voltage with the at least one electrode; and
determining, based on the at least one sensed voltage, an impedance of the at least one electrode of the first instrument.

* * * * *